United States Patent [19]

Stevens et al.

[11] Patent Number: 5,105,822
[45] Date of Patent: Apr. 21, 1992

[54] APPARATUS FOR AND METHOD OF PERFORMING HIGH FREQUENCY AUDIOMETRY

[75] Inventors: Kenneth N. Stevens, Cambridge, Mass.; David M. Green, Gainsville, Fla.; Robert A. Berkovitz, Belmont, Mass.

[73] Assignee: Sensimetrics Corporation, Cambridge, Mass.

[21] Appl. No.: 156,299

[22] Filed: Feb. 16, 1988

[51] Int. Cl.$^5$ .............................................. A61B 5/00
[52] U.S. Cl. ..................................... 128/746; 73/585; 73/587
[58] Field of Search ...................... 128/746, 420.5, 421, 128/783, 784, 789; 73/645–648, 585, 587, 589, 591; 381/71, 72, 151–155, 158; 600/25; 181/128, 129, 130–137

[56] References Cited

U.S. PATENT DOCUMENTS 4,601,295 7/1986 Teele .................................. 128/746

OTHER PUBLICATIONS

Green et al., "High Frequency Audiometric Assessment of a Young Adult Population", Feb. 1987.
Stevens et al., "Calibration of Ear Canals for Audiometry at High Frequencies", Feb. 1987.

Primary Examiner—Lee S. Cohen
Assistant Examiner—J. P. Lacyk
Attorney, Agent, or Firm—Hale and Dorr

[57] ABSTRACT

An apparatus for and method of applying a selected range of high frequency acoustic energy to the apical end of the eardrum of an ear canal at a predetermined, substantially absolute sound pressure level at any frequency in the range of interest. The selected range of frequencies is generated at a location remote from the ear canal and the sound pressure level of each frequency is varied at the time of generation in accordance with a calibration function to ensure the frequencies reaching the apical end of the eardrum are at the predetermined sound pressure level.

The calibration function is calculated by transmitting an acoustic pulse of broad frequency spectrum into the ear canal, measuring the sound pressure of the transmitted acoustic pulse and reflection thereof adjacent the entrance of the ear canal, and removing from the spectrum of the measured sound pressure the destructive interference effects between the transmitted and reflected acoustic pulses. The resultant sound pressure level contains nonuniformities having information regarding the sound transmission characteristics of the ear canal and the acoustic pulse generation and transmission system from which the calibration function is calculated.

55 Claims, 8 Drawing Sheets

APPARATUS FOR AND METHOD OF PERFORMING HIGH FREQUENCY AUDIOMETRY

The present invention pertains to apparatus for and methods of measuring hearing at high frequencies, and more particularly to an apparatus for and method of providing acoustic sinusoidal signals at the apical end of the ear drum of an ear canal at predetermined sound pressure levels regardless of frequency.

Until recently, little interest existed in the measurement of human hearing at high frequencies (above 8,000 Hz), as partial or total loss of hearing at these high frequencies has little effect on an individual's ability to understand speech, enjoy music, or pursue most occupations successfully. Thus, little motivation existed for developing methods of measuring hearing at high frequencies. Consequently, and for technical reasons discussed hereinafter, known high frequency audiometry methods and apparatus have typically been inaccurate and unreliable.

In recent years, it has become clear that the deterioration of hearing at high frequencies may provide a first indication of the toxic effects of industrial chemicals, medications, and other substances to which people might be exposed. To detect such changes in high frequency hearing sensitivity it is necessary to measure accurately and reliably hearing at high frequencies.

The difficulty in accurately measuring hearing sensitivity at high frequencies arises primarily from the fact that the wavelength of sound at frequencies above 8,000 Hz is comparable to the dimensions of the auditory canal. As a result, standing waves form in the ear canal when sound at a high frequency is presented to the ear. In such case, at some locations in the ear canal the sound pressure is very high, while at others it may be vanishingly small. While these variations typically do not affect the sound pressure at the eardrum, they do make it extremely difficult to calibrate an audiometer at high frequencies, that is to establish with certainty the sound pressure actually presented to an individual's eardrum. Absent such accurate calibration, it is extremely difficult to conduct precise audiometry at high frequencies.

Accurate high frequency audiometry is also difficult to achieve because of the geometry of an individual's ear canal. The gradual inward taper of most ear canals produces at the eardrum a relative elevation of the sound pressure level of higher frequency sounds, which elevation varies with the degree of tapering. In addition, most ear canals are curved slightly along their long axis, and the eardrum of most ear canals is inclined with respect to the long axis. These configurations also affect the sound pressure of high frequency sounds at the apical end of the eardrum.

One method of overcoming the above-discussed factors would be to measure the sound level with a small microphone directly at a subject's eardrum. Measurements of this kind have been made in research laboratories. Such a method, however, is highly undesirable in view of the risk of injury attendant with insertion of a miniature microphone in the subject's ear canal at a position adjacent the eardrum.

Another method of measuring hearing at high frequencies involves the use of a model ear canal or coupler. Acoustic energy is transmitted into the model ear canal and measurements are made of the sound pressure level at the location in the coupler corresponding to the eardrum. The relationship between the sound pressure levels provides a calibration function for the model ear canal that is used in high frequency hearing measurement of live subjects.

At frequencies below 8 kHz, where the wavelength of sound is significantly greater than the length of an ear canal, this technique provides reasonably accurate calibration. At frequencies above about 8 kHz, however, the wavelength of sound approximates the dimensions of an ear canal. As a result, standing waves are formed in the ear canal or coupler which perturb the sound transmission pattern of the ear canal or coupler so as to make calculation of an accurate calibration function difficult if not impossible. Unfortunately, in view of the above-discussed geometric and other non-uniformities in actual human ear canals, the calibration function for the model ear canal typically varies significantly at high frequencies from the calibration function for an actual human ear canal. As a result, this high frequency audiometry technique has typically been quite unreliable.

Still another method of calibrating an audiometer at high frequencies is described by M. A. Krasner, K. N. Stevens, D. M. Green, and S. H. Blumenthal in the paper "Development of a Technique for High Frequency Audiometry", presented at the International Conference on Acoustics, Speech, and Signal Processing, in Boston, Mass., on Apr. 14–16, 1983. In this technique, acoustic energy is delivered from an acoustic source mounted in a headphone positioned over the subject's ears. A small microphone is located in the earpiece for measuring (a) the sound pressure of the acoustic energy transmitted from the acoustic source and (b) reflections of the transmitted acoustic energy from the eardrum of the subject's ear canal. A calibration function relating sound pressure at the eardrum of the ear canal to excitation voltage at the acoustic source is calculated from the sound pressure measured at the microphone using the two following techniques.

The first technique involves identifying the poles of the ear canal system using a peak-finding algorithm and then estimating an all-pole transfer function for the ear canal relating sound pressure at the eardrum to the excitation voltage applied to the sound source. The second technique involves identifying the zeros of the ear canal system and then estimating an all-zero transfer function. The measured pole-zero spectrum is then inverse filtered to remove the effect of the zeros, leaving an estimate of the transfer function from source to eardrum. In performing a hearing sensitivity measurement, sound pressure is varied at the acoustic source in accordance with the calibration function, and if the latter is accurate the sound pressure at the eardrum will be substantially constant across the frequency range of interest.

The use of a headphone for containing the acoustic source and microphone reduces significantly the accuracy of the Krasner, et al. technique, however, inasmuch as the headphone tends to reflect back the acoustic energy reflected by the eardrum. This reflection creates additional standing waves in the ear canal which interfere with the existing sound wave transmission pattern of the ear canal. Such interference reduces significantly the accuracy of the calibration function and increases the complexity of calculating the calibration function. Another problem with the Krasner, et al. technique is that the headphone must be substantially totally immobilized with respect to the ear canal to obtain accurate audiometric results. Practically speaking, such immobilization is very difficult to achieve.

A technique similar to the one disclosed by Krasner, et al., was described by D. M. Green, K. N. Stevens, R. Berkovitz, A. Derr, M. Krasner, and R. Pyle in an abstract entitled "A Procedure for Calibrating Ear Canals at High Frequencies", published in the Journal of the Acoustical Society of America Supplement 1, vol. 75, spring 1984, page S11. In the Green, et al. technique, sound is supplied to the ear canal entrance via a tube coupled to the acoustic source, and the acoustic source at the ear canal entrance had an impedance close to $\rho c$, where $\rho$ equals the density of air at standard pressure and temperature, and c equals the speed of sound at standard pressure and temperature. The Green, et al. technique was tested and the results of the test were reported in an abstract by G. Kidd, Jr., R. Berkovitz, K. N. Stevens, and D. M. Green entitled "Hearing Thresholds at High Frequencies: Results Obtained Using a New Measurement Technique", published in the Journal of the Acoustical Society of America Supplement 1, vol. 77, spring 1985, page S62.

While the methods of Krasner, et al., and Green, et al. are designed to overcome the high frequency calibration problems detailed above, these methods still do not provide a calibration function having the accuracy desired for certain high frequency audiometry.

An object of the present invention is to provide an apparatus for and method of calculating a calibration function for a human ear canal relating the spectrum of an excitation signal applied to a sound source for generating an acoustic pulse to the sound pressure level of the acoustic pulses at the apical end of an eardrum.

Another object of the present invention is to provide an apparatus for and method of removing from a response signal generated by the reflection from an eardrum of an acoustic pulse the destructive interference effects created by the interaction of the incoming acoustic pulse with the reflected acoustic pulse.

Yet another object of the present invention is to provide an apparatus for and method of providing a calibration function for an individual human ear canal in which acoustic waves reflected from the ear canal, propagated back to the source that generated the acoustic waves, reflected from the source, and propagated back toward the ear canal are dissipated before intercepting the ear canal again so as to avoid the introduction of additional standing waves to the wave transmission pattern of the ear canal.

Yet another object of the present invention is to provide an acoustic sinusoidal signal over a frequency range of interest at the apical end of the eardrum of the ear canal so that the sound pressure level of the acoustic frequencies is accurately known regardless of frequency.

These and other objects are achieved in an apparatus for and method of generating and transmitting an acoustic sinusoidal signal over a frequency range of interest to the apical end of the eardrum of an ear canal so that the sound pressure level thus provided at such apical end is at a substantially predetermined level regardless of frequency. The apparatus comprises a sound source for generating high-frequency sound of selected amplitude, spectral content and duration, a resilient elongated hollow, coupling tube and earpiece for transmitting the sound pressure from the sound source to the apical end of the eardrum through a substantially sealed acoustical transmission line comprising the tube, earpiece and ear canal, the coupling tube being sufficiently lossy by virtue of its resilience to attenuate substantially all reflections directed toward the sound source, a microphone positioned near the entrance of the ear canal for detecting transmitted and reflected sound, and a signal processing device coupled to the sound source and microphone for calculating a calibration function for the ear canal of interest relating sound pressure level at the apical end of the eardrum with the excitation signal applied to the sound source.

To calculate the calibration function, an excitation signal is applied to the sound source causing the latter to generate a sound which is transmitted through the coupling tube and earpiece to the ear canal. The sound propagates in the ear canal until reaching the ear drum, where the sound is reflected and retransmitted back out the ear canal. The microphone receives both the originally transmitted and the reflected sound. The coupling tube and sound absorbent material positioned in the sound source attenuate the reflection sufficiently so that the latter will not propagate back to the sound source, reflect from the sound source, and propagate back into the ear canal. A signal processing procedure is performed by the signal processing device which removes from the spectral magnitude of the response signal received at the microphone the effects of wave interference between the transmitted and reflected acoustic energy so as to provide a signal containing only non-uniformities introduced by the sound source and transmission system as modified by the geometric configuration and other characteristics of the ear canal. This signal is used as a calibration function for the ear canal of the subject being tested.

The signal processing procedure involves taking the Fourier transform of the impulse response generated by the microphone to provide a first spectrum, calculating the center frequencies and bandwidths of the zeros in the first spectrum, generating a time domain coefficient list representing the zeros in the first spectrum, taking the Fourier transform of the time domain coefficient list to generate a second spectrum, determining the log power spectrum of the first and second spectrum, and subtracting the log power spectrum of the second spectrum from the log power spectrum of the first spectrum to provide a resultant function which represents the specific acoustic transmission characteristics of the ear canal.

After the calibration function has been generated, the sensitivity of the subject to sound of selected high frequencies can be determined by continuously adjusting the amplitude of the test sound generated at the sound source in accordance with the calibration function so that the sound present at the eardrum is of known sound pressure level regardless of the frequencies transmitted. For example, by step-wise increasing the level of the sound frequencies transmitted, and monitoring when the subject first detects the sound, a profile of the subject's hearing thresholds for high frequency sounds can be generated.

For a fuller understanding of the nature and objects of the present invention, reference should be had to the following detailed description taken in connection with the accompanying drawings wherein.

Figure 1:
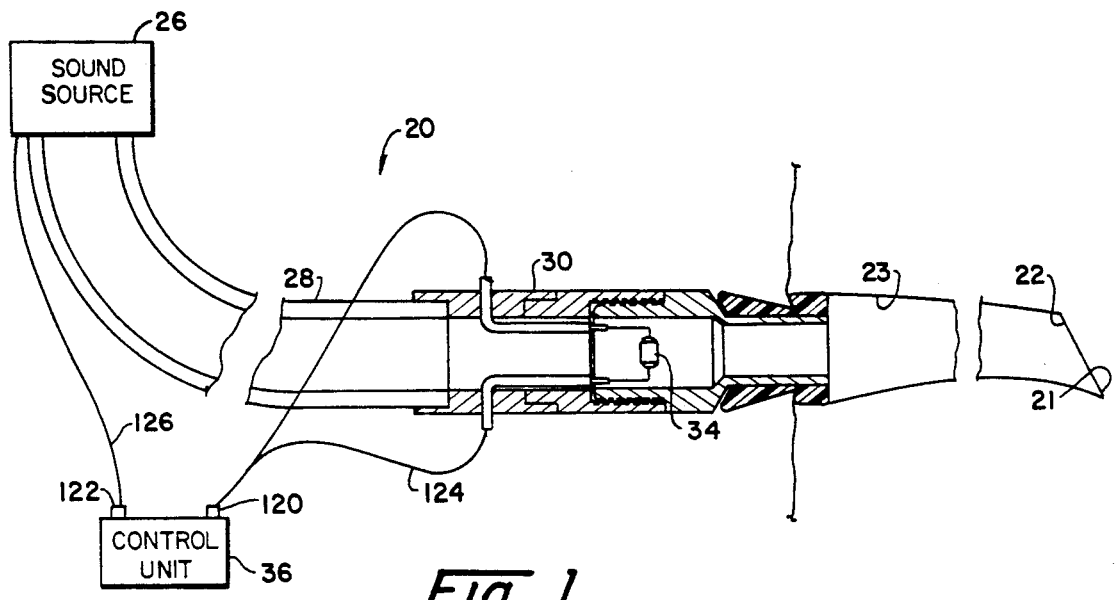
FIG. 1 is a schematic representation of the high frequency audiometry device of the present invention.
Figure 1A:
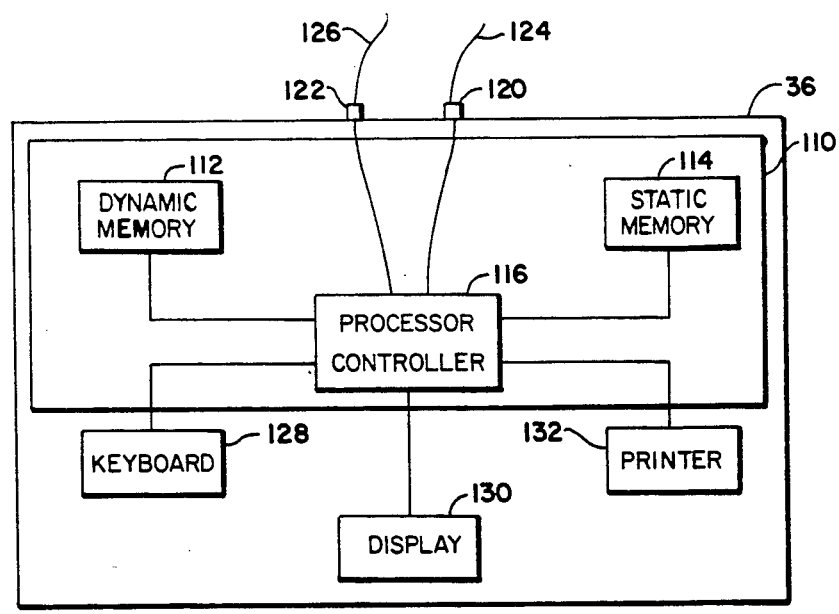
FIG. 1a is a schematic representation of the control unit.

Referring now to FIG. 1, the present invention comprises an apparatus 20 for providing a selected spectrum of high frequency acoustic energy at the apical end 21 of the eardrum 22 of an individual's ear canal 23 at a predetermined sound pressure level regardless of frequency. As discussed above, the cross section of ear canal 23 decreases, as measured along the length thereof from the ear canal entrance to eardrum 22. The latter is typically inclined with respect to the longitudinal axis of ear canal 23.

Briefly, the apparatus 20 comprises a sound source 26 for generating acoustic sinusoidal signals in a frequency range of interest, and of selected duration and amplitude, and a tube 28 and earpiece 30 for delivering the sound to the entrance of the ear canal 23. A microphone 34 is disposed in earpiece 30 for detecting acoustic energy transmitted from sound source 26 and acoustic energy reflected off eardrum 22. A control unit 36 is connected to sound source 26 and microphone 34 for calculating a calibration function for ear canal 23 and for controlling the operation of sound source 26 in accordance with the calibration function so as to generate a predetermined spectrum of sound which when received at apical end 21 of ear canal 23 is of predetermined sound pressure level across the predetermined frequency spectrum regardless of frequency.

Figure 2:
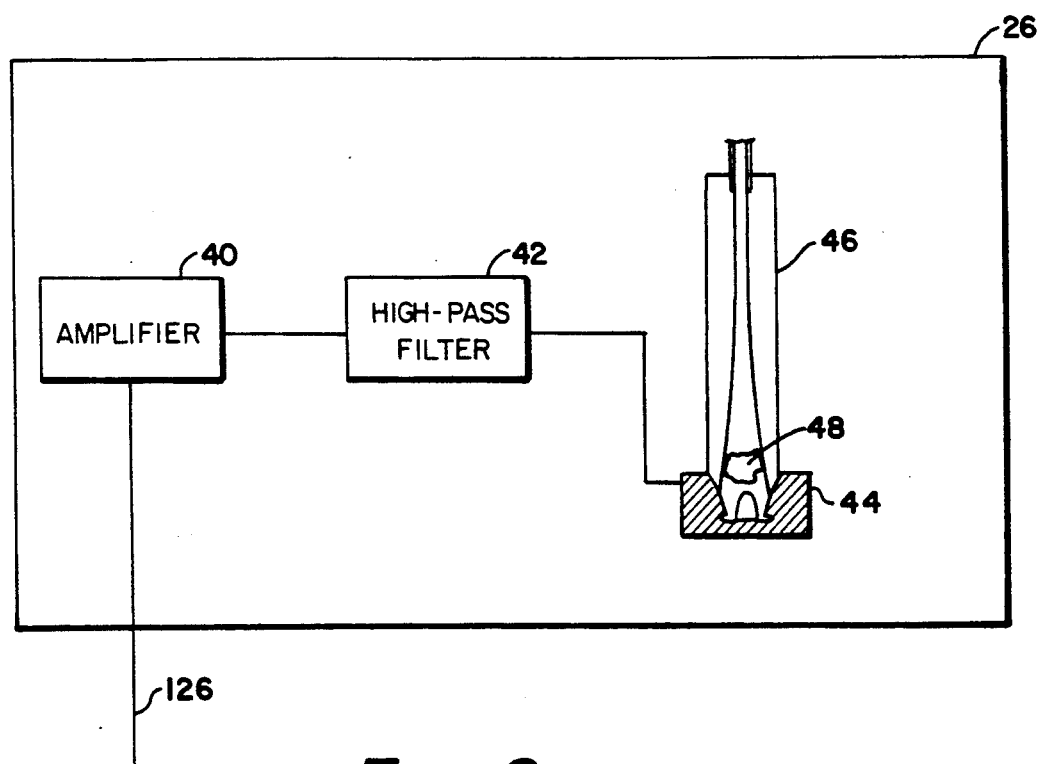
FIG. 2 is a schematic representation of the sound source.

Sound source 26 is provided for generating high-frequency, i.e., 8-20 kHz, acoustic sinusoidal signals of selected sound pressure and frequency. Referring to FIG. 2, sound source 26 comprises an amplifier 40, a high-pass filter 42, and a driver 44 which is coupled to filter 42. Source 26 includes a horn 46 which is acoustically coupled with driver 44. A conventional power amplifier may be employed as amplifier 40. High-pass filter 42 preferably has a cut-off frequency of about 7 kHz and a gently sloping response below the cut-off frequency. High-pass filter 42 is provided to prevent low-frequency noise from reaching driver 44. The latter is a high-frequency transducer capable of generating a sound pressure level of approximately 130 dB at the eardrum across the frequency range of interest. In addition, the output of driver 44 should be relatively free of harmonic distortion and broadband noise. A suitable driver 44 is sold by Radio Shack Corporation under the name Radio Shack Super Tweeter, model 40-1310A. Horn 46 is a reverse catenoidal horn. The latter is inserted between driver 42 and coupling tube 28 for coupling the driver to the tube.

Preferably, sound absorbent material 48 (FIG. 2) is positioned in horn 46 or near the diaphragm of driver 44 to aid in attenuating acoustic energy reflected out of ear canal 23, as described in greater detail below. A variety of materials, including absorbent cotton, absorbent foam or urethane foam may be used as sound absorbent material 48, the only requirements being that the material not totally attenuate acoustic energy transmitted from driver 44 such that the energy never reaches ear canal 23 and that the material provide a satisfactory degree of attenuation.

Tube 28 is a lossy waveguide for transmitting acoustic energy from driver 44 and horn 46 to the entrance of ear canal 23. Tube 28 is a hollow, resilient tube, typically rubber or some soft plastic of selected length, internal cross-section, and durometer. These three parameters are balanced so that the principal modes of the sound generated at driver 44 will propagate in the atmosphere enclosed in the hollow interior of the tube 28 along its length toward the ear canal 32. These three parameters are further selected so that the tube, together with absorptive material 48, if used, will substantially entirely attenuate a by absorption, all sound reflected off the eardrum of the ear canal, transmitted back into tube 28, and reflected off sound source 26 before the twice reflected sound reaches microphone 34. In addition, the three parameters are balanced so that the acoustic impedance of tube 28 as seen from the ear canal is equal to $\rho c/A$, where $\rho$ is the density of air at standard pressure and temperature, c is the speed of sound at standard pressure and temperature, and A is the cross-sectional diameter of the hollow interior of the tube.

An exemplary tube 28 has an internal diameter of $\frac{1}{4}"$, a length of 650 mm and a durometer believed to range from 35 to 65. The acoustic impedance of such a tube is believed to be about 125 acoustic ohms in CGS units. A tubing meeting these parameters is identified under the mark TYGON®, model no. B-44-4X. This tubing meets the 3A plastics standard for processed milk service. Of course, other tubing of varying length and internal diameter may be satisfactorily employed, so long as the tubing transmits the principal modes of the sound generated at driver 44 while also absorbing or dissipating via transmission through the wall of the tube substantially all sound reflected off the eardrum 22 of the ear canal 23, transmitted back into tube 28, reflected from sound source 26, and transmitted back toward the ear canal before the twice-reflected sound reaches microphone 34.

Figure 1B:
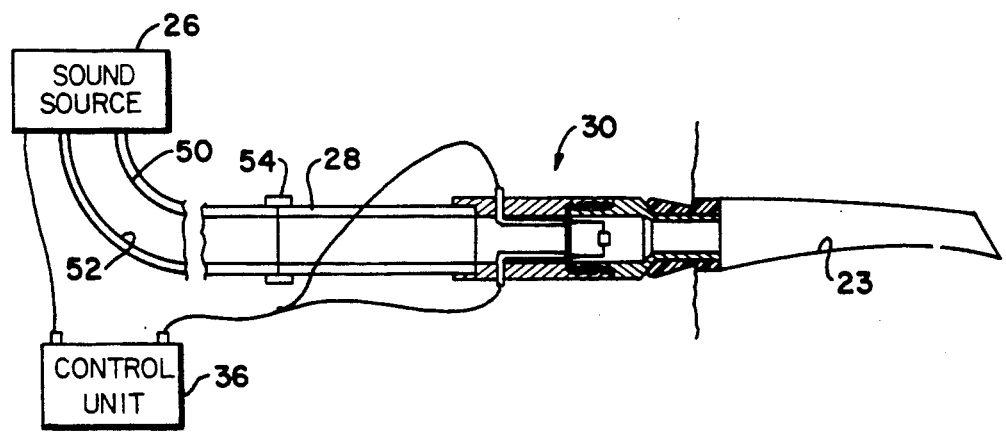
FIG. 1b is a schematic representation of another embodiment of the acoustic transmission tube shown in FIG. 1.

Referring next to FIG. 1b, in certain circumstances it may be desirable to couple a rigid tube 50 to flexible tube 28 so as to increase the distance between sound source 26 and ear canal 23. Tube 50 has a hollow interior 52 with an inside diameter at the end of the tube that is coupled with tube 28 that is approximately equal to the inside diameter of tube 28 at the end thereof that is couplable with tube 50. This inside diameter of tube 50 is selected so that a substantially continuous acoustic transmission path is formed at the junction of tubes 28 and 50. Tubes 28 and 50 are coupled together by a clamp 54.

As illustrated in FIG. 1b, rigid tube 50 is coupled to sound 26 and flexible tube 28 is coupled to earpiece 30. In the alternative, flexible tube 28 can be coupled to sound source 26 and rigid tube 50 coupled to earpiece 30.

Tube 50 is provided for increasing the spacing between sound source 26 and ear canal 23 so as to make it easier for the audiologist using the system 20 to perform the calibration function calculation and subsequent high frequency audiometry. Tube 50 is made from a rigid material so that acoustic signals can be transmitted in its hollow interior substantially without loss.

Figure 3:
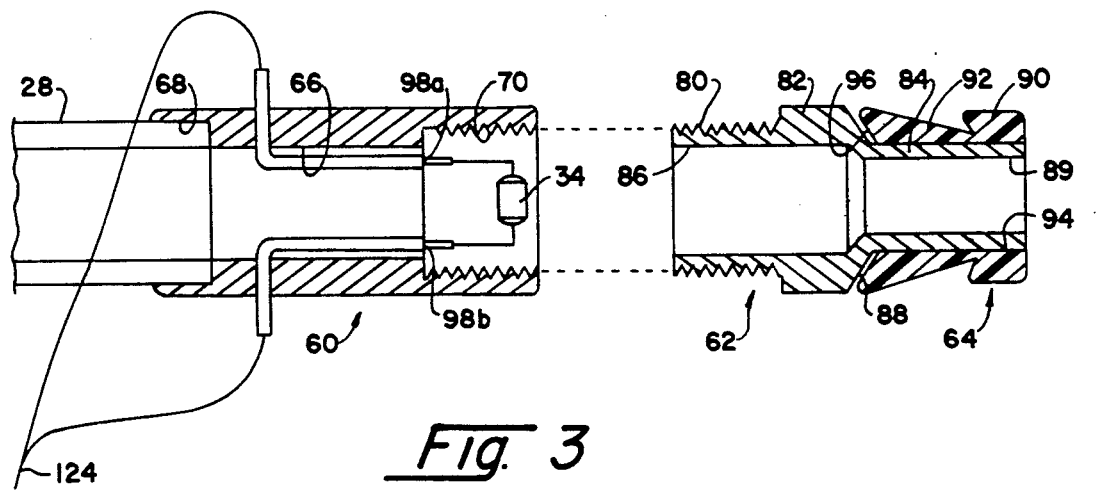
FIG. 3 is a longitudinal, cross-sectional view of the earpiece.

Referring now to FIG. 3, earpiece 30 comprises coupler 60, intermediate portion 62, and tip 64. Coupler 60 has a cylindrical shape and comprises a central bore 66 having a smooth counterbore 68 at one end and a threaded counterbore 70 at the other end. The diameter of bore 66 is substantially identical to the inside diameter of tube 28. The diameter of counterbore 68 is slightly less than the outside diameter of tube 28 so that the distal end of the latter can be received with a friction fit in counterbore 68. Threaded counterbore 70 has a diameter and thread pitch selected to permit threaded end 80 of intermediate portion 62 to be threadably received therein, as discussed below.

Intermediate portion 62 has a generally cylindrical configuration and comprises threaded end 80, central section 82, reduced diameter portion 84, and central bore 86. The diameter of central bore 86 is substantially identical to the diameter of central bore 66 in coupler 30. Threaded end 80 has an outside diameter and thread pitch selected to permit the latter to be threadedly disposed in threaded counterbore 70. Central section 82 includes a transversely-extending surface 88 extending upwardly from the junction of reduced diameter portion 84 and central section 82. Reduced diameter portion 84 is rigidly attached to the remainder of intermediate portion 62, and portion 84 has a relatively smooth, cylindrical outer surface of selected diameter. Portion 84 includes a central bore 89 that is coaxially aligned with bore 86 in intermediate portion 62. The diameter of bore 89 is selected to be approximately equal to the diameter of the subject's ear canal at the entrance thereto, and so typically has a diameter that is slightly less than the diameter of bore 86. A smoothly-tapering surface is provided at the junction of the bores 86 and 89.

Tip 64 is designed to be removably insertable into the entrance of an ear canal 23, and to provide a substantially acoustically-tight coupling between earpiece 30 and the ear canal when tip 64 is inserted in the entrance to the ear canal. Tip 64 includes a circular flange 90 at the front of the tip, and a gradually-tapering frusto-conically shaped section 92, the narrow end of which intersects flange 90. The outside diameter of flange 90 and frusto-conically shaped section 92 will vary depending upon the size of the ear canal into which the tip 64 is to be inserted. Section 92 terminates in a transversely-extending end 96 that is configured to engage transversely-extending surface 88 on intermediate portion 62. Tip 64 has a central bore 94 having a diameter selected so that the former will engage reduced diameter portion 84 with a friction fit when the tip is positioned thereon. Tip 64 is preferably made from a relatively soft, elastic material.

Microphone 34 may be disposed inside coupler 60 and is provided for detecting the sound pressure level of transmitted and reflected sound inside the coupler 60. Preferably, microphone 34 has an essentially flat frequency response ($\pm 1$ dB), and has a sensitivity of at least about $-121$ dB re: 1 V per dyne/cm$^2$. Microphone 34 is much smaller than the diameter of bore 66 in coupler 60 so the microphone does not introduce irregularities of significant magnitude to the sound transmitted through earpiece 30 into the ear canal. In the event microphone 34 is disposed inside coupler, as illustrated in FIG. 3, the length of microphone 34, as measured along any of its axes, is preferably about one quarter of the inside diameter of tube 28. Thus, for instance if the diameter of central bore 66 in coupler 60 is 0.25 inches, the length and diameter of microphone 34 will be on the order of about 0.0625 inches long and 0.0625 inches thick. A suitable microphone 34 can be manufactured from a product sold by Vernitron Piezo-Electric Division, Bedford, Oh., under the product name PZT-4 ceramic cylinder #1-1010-4.

Microphone 34 is mechanically and electrically connected to coupler 60 via a pair of electrically-conductive struts 98a and 98b. One end of strut 98a is attached to and extends through the sidewall of coupler 60 and the opposite end of strut 98a is attached to one end of microphone 34. One end of strut 98b is attached to and extends through the sidewall of coupler 60 in diametric opposition to the one end of strut 98a. The opposite end of strut 98b is attached to the other end of microphone 34.

It will be appreciated that the hollow interior of tube 28, together with bore 66 and 86 and ear canal 23 form a closed chamber or acoustic transmission line for propagating sound waves through the gaseous medium enclosed in the chamber, inasmuch as the coupling provided by ear piece 30 serves to substantially seal the chamber.

Figure 3A:
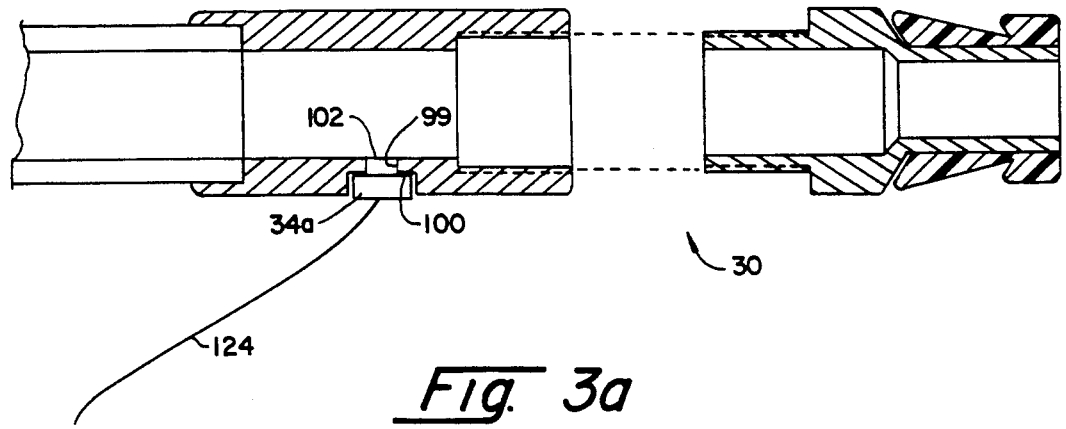
FIG. 3a is a longitudinal cross-sectional view of another embodiment of the earpiece.

Referring now to FIG. 3a, in another embodiment of earpiece 30, a microphone 34a is secured to the outside wall of coupler 60 instead of being suspended inside the coupler on struts 98. To achieve this mounting arrangement, an aperture 99 is provided in coupler 60, and a cavity 100 is provided in the sidewall of coupler 60 intersecting aperture 99 for receiving microphone 34a. Coupler 60 includes an acoustic port 102 having a hollow interior and two open ends for transmitting acoustic energy present in bore 66 to the diaphragm (not shown) of microphone 34a. Acoustic port 102 is sized to fit tightly in aperture 99.

One end of acoustic port 102 is secured to the body of microphone 34a so that the hollow interior of the port is in acoustic communication with the diaphragm of the microphone. The other end of acoustic port 102 is slightly curved so that when the port is disposed as desired in aperture 99, the other end will be flush with, and have the same radius of curvature as, the wall of bore 66. By this flush mounting of the acoustic port 102, substantially no irregularities are introduced to acoustic energy transmitted in bore 66. The acoustic transmission characteristics of acoustic port 102 are selected so that substantially no irregularities are introduced to acoustic energy transmitted through the port to microphone 34a. In every other way, microphone 34a can be substantially identical to microphone 34 illustrated in FIG. 3.

A conventional hearing-aid microphone may be satisfactorily employed as microphone 34 and acoustic port 102. In such a device the acoustic port and microphone typically form an integral assembly. A hearing-aid microphone of this type is sold by Knowles Electronics, Inc. of Franklin Park, Ill. and is identified by model number 1954.

An advantage of the microphone arrangement illustrated in FIG. 3a is that cross modes in the acoustic energy propagated in bore 66, if present, will not be apparent at the wall of the bore inasmuch as the waves in the acoustic energy are in phase at the wall of the bore. As such, the sound pressure measured by microphone 34a is not affected by the cross modes.

Figure 3B:
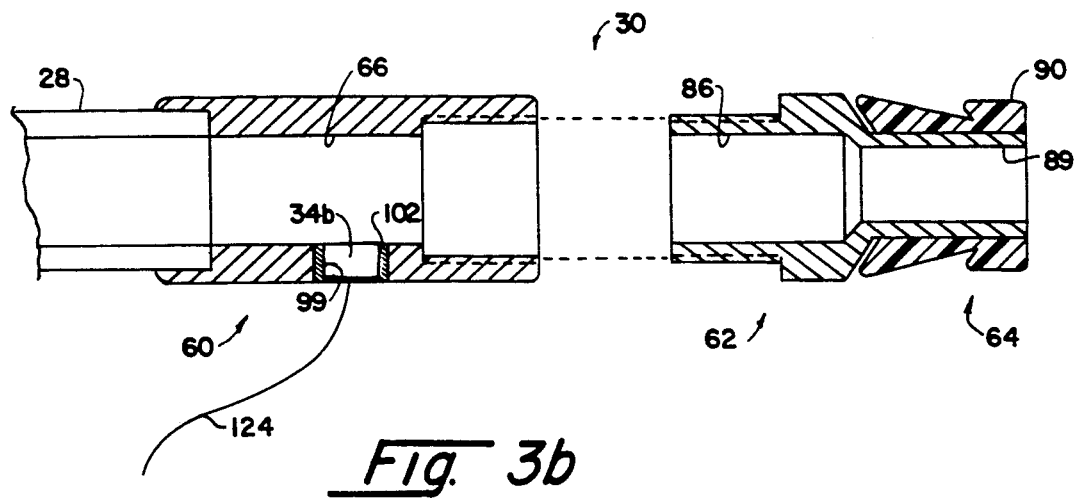
FIG. 3b is a longitudinal, cross-sectional view of another embodiment of the earpiece.

Referring now to FIG. 3b, in another embodiment of earpiece 30, instead of spacing the diaphragm of microphone 34a from bore 66 and coupling the former with bore 66 via acoustic port 102; aperture 99 and acoustic port 102 may be enlarged so that the diaphragm of the microphone is coextensive with the wall of bore 66, as illustrated in FIG. 3b. By this positioning of microphone 34b, fewer cross modes are generated inside bore 66 than with microphone 34 which is suspended on struts 98 inside bore 66, and any cross modes present in the acoustic energy in bore 66 will not be apparent to the microphone 34b for the reasons discussed above with respect to microphone 34a. As such, fewer irregularities are introduced into the output signal of the microphone 34b, with the result that the calculation of the calibration function of the ear canal is simplified. In every other respect, the microphone 34b of FIG. 3b can be substantially identical to the microphone 34a of FIG. 3a.

Figure 3C:
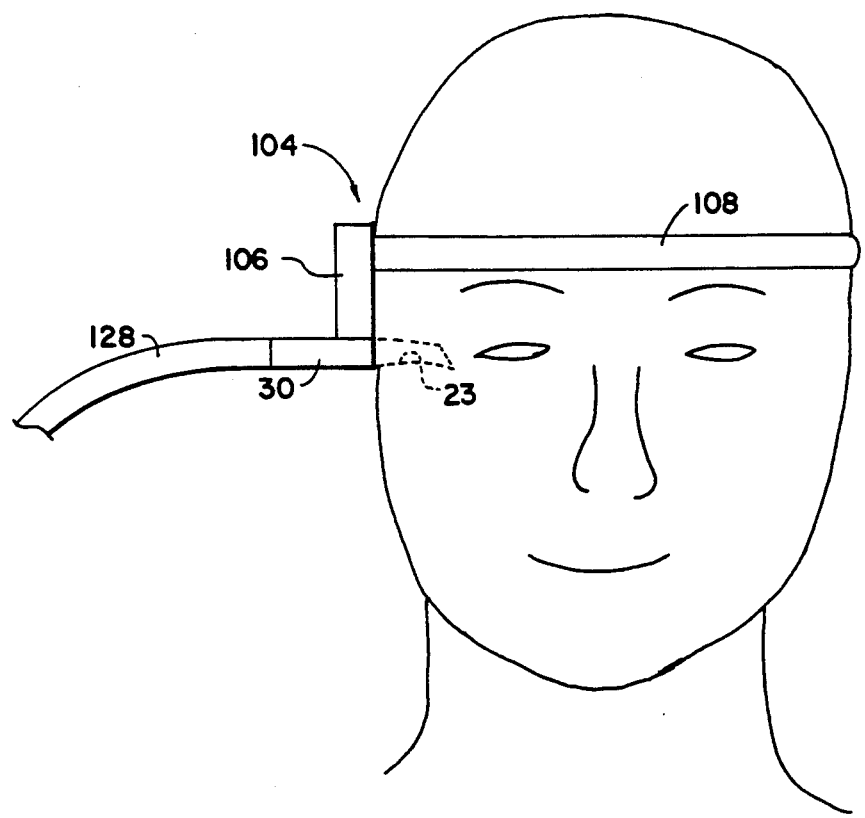
FIG. 3c is a schematic representation of the headpiece assembly.

Referring next to FIG. 3c, the system 20 of the present invention preferably comprises a headpiece assembly 104 for supporting earpiece 30 in substantially fixed relationship to ear canal 23. Headpiece assembly 104 comprises headband 106 and adjustment fixture 108 secured to the headband. The latter is adjustable to fit snuggly around the head of the subject undergoing audiometry. Adjustment fixture 108 is releasably couplable with earpiece 130 and is adapted to move the latter through all three axes relative to ear canal 23. Thus, by proper manipulation of adjustment fixture 108, earpiece 30 can be properly and securely located relative to ear canal 23. As skilled practitioners will appreciate, headpiece assembly 104 may have any number of suitable configurations, the only requirements being that the headpiece assembly support securely the earpiece 30 relative to the ear canal 23 and the headpiece assembly permit adjustment of the earpiece 30 in all three axes relative to the ear canal.

Control unit 36 is provided for calculating a calibration function for the ear being tested by processing the output signal received from microphone 34 through a multi-step signal processing procedure, as illustrated in FIGS. 4–9, and for generating acoustic sinusoidal signals in accordance with the calibration function for use in performing high frequency audiometry. Control unit 36 comprises a digital, programmable control computer 110. The latter includes dynamic memory 112, static memory 114, and processor/controller 116.

Static memory 112 is provided for storing the various signal processing algorithms used in calculating the calibration function, the algorithms for controlling the operation of the sound source 26, during high frequency audiometry, and other algorithms use in controlling the operation of control unit 36. Dynamic memory 114 is provided for temporarily storing data received from microphone 34 and data to be transmitted to sound source 26, and for storing information used by processor/controller 116 in executing the algorithms stored in dynamic memory 112 and controlling the operation of control unit 36. Processor/controller 116 is provided for executing the calculations of the algorithms stored in dynamic memory 112 using data stored in static memory 114, and for controlling the sequence in which information enters and leaves the computer 110. The latter preferably has a dynamic memory consisting of storage units of at least 16 bits, a static memory consisting of storage units of at least 16 bits, and a clock speed of at least 20 MHz. An exemplary microprocessor that can be satisfactorily employed as the CPU of computer 110 is manufactured by Motorola Incorporated of Phoenix, Ariz., and is identified by model number DSP56000.

Control unit 36 also includes an input port 120 for receiving the output signal from microphone 34 and an output port 122 for providing an excitation signal to sound source 26. Input port 120 is electrically connected over line 124 to the output of microphones 34, 34a, or 34b, depending upon which embodiment of earpiece 30 is employed. Output port 122 is electrically connected over line 126 to amplifier 40 of sound source 26.

Control unit 36 further comprises a keyboard 128, a display 130, and a printer 132. These elements are connected to processor/controller 116 of computer 110. Information regarding the amplitude, duration, and spectral content of the acoustic pulses and acoustic sinusoidal signals generated by sound source 26, and other factors relating to the calculation of the calibration function and generation of the acoustic sinusoidal signals used in performing high frequency audiometry, are entered into control unit 36 via keyboard 128. The information entered via keyboard 128 to computer 110, and information generated pertaining to the calibration function and performance of high frequency audiometry, are displayable on display 130 and printer 132.

Prior to performing high frequency audiometry, a calibration function must be calculated which equates the magnitude of the excitation signal provided to sound source 26 with the absolute sound pressure level of acoustic sinusoidal signals transmitted to the apical end of the eardrum of the ear canal. This calibration function is calculated based on the information contained in the output signal of microphones 34, 34a or 34b using signal-processing algorithms stored in dynamic memory 112. To obtain information needed for calculating the calibration function, an acoustic pulse of selected duration, pressure, and spectral content is generated at sound source 26 and is transmitted in tube 28 to ear canal 23. Microphone 34, 34a or 34b receives this pulse and reflections thereof and generates an output signal in response thereto, as illustrated at 130 in time domain in FIG. 4. It is to be appreciated that the sound field in tube 28 is substantially evenly distributed throughout the tube except where such even distribution is affected by destructive interference caused by interaction between the transmitted and reflected acoustic pulses. This output signal 130 includes spectral non-uniformities introduced from the sound source 26, tube 28, earpiece 30, the configuration of ear canal 23, and the interference pattern generated by the interaction between the transmitted acoustic pulse and reflections thereof from eardrum 22 of the ear canal.

Figure 4:
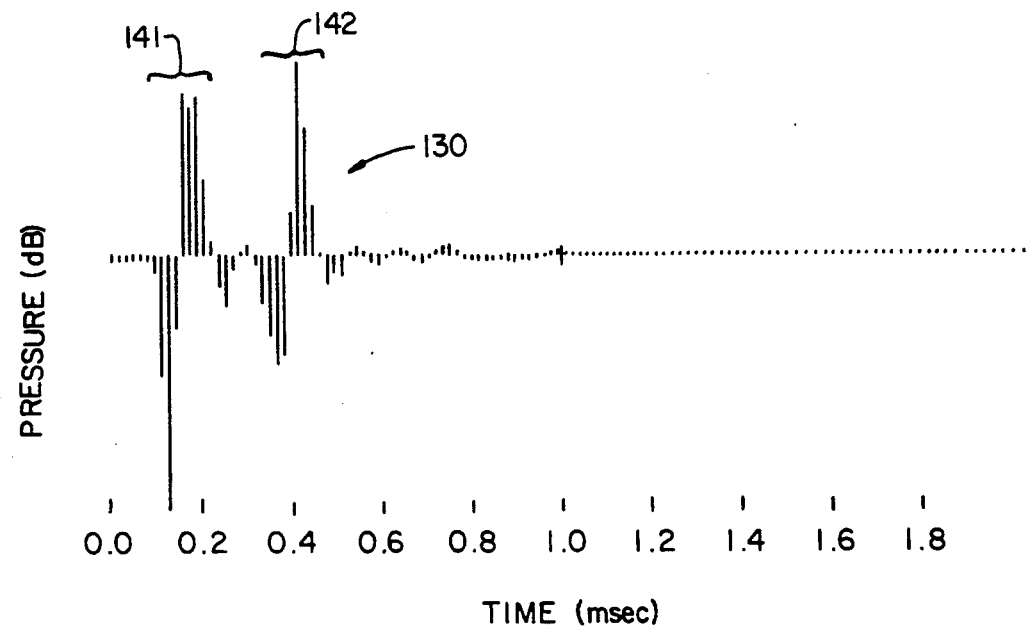
FIG. 4 is a graph in the time domain of the pulse signal received at the microphone.
Figure 5:
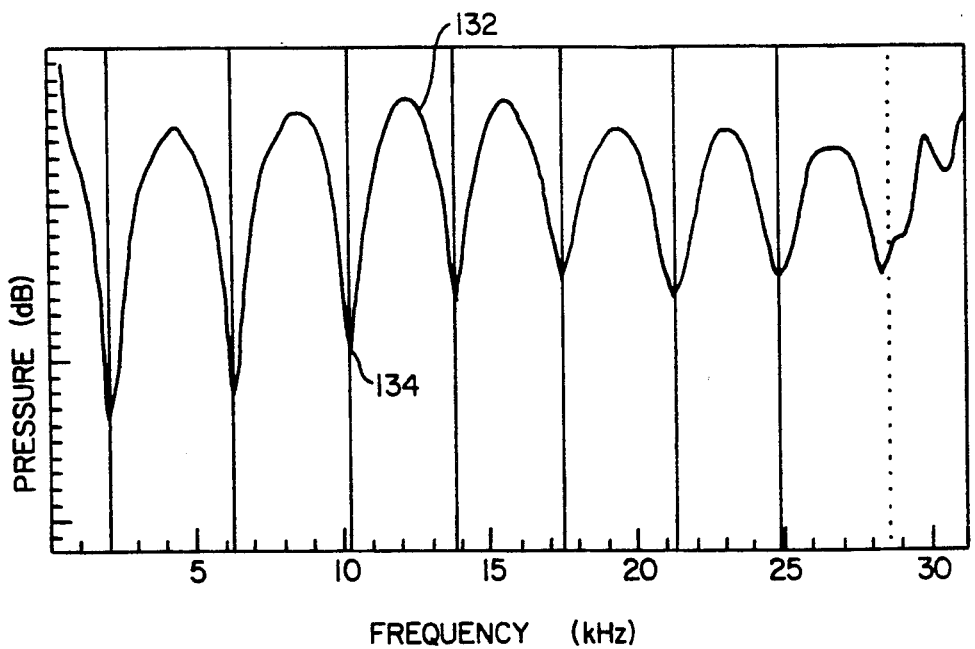
FIG. 5 is a graph of a Fourier transform of the pulse signal of FIG. 4.

As the first step in calculating the calibration function, the Fourier transform of signal 130 of FIG. 4 is taken which produces a list or set 132 of the amplitudes of each frequency represented in signal 130, as illustrated in FIG. 5. This list 132 contains the spectral non-uniformities present in the initial pulse signal 130 of FIG. 4, and comprises a discrete collection of points, the number and spacing of which is a function of the sampling rate and the number of samples transformed. Preferably, a sampling rate of 60 kHz and amplitude resolution of at least 12 bits are used and the Fourier transform is computed on the basis of 512 samples. Each point represents the magnitude of the relative energy of a specific frequency in the list 132. Preferably, a conventional fast Fourier transform, e.g., a transform using the Cooley-Tukey algorithm or other suitable algorithm, is employed to generate the spectral list 132 of FIG. 5. The latter has a comb-like configuration and includes a plurality of irregularly-spaced minima or zeros 134. The zeros exist at the frequencies of maximum destructive interference.

From the spectral list 132, the center frequencies and bandwidths of the minima or zeros 134 are calculated. This calculation is performed by first comparing each discrete point on the spectral list 132 with its immediate neighbors and then labeling the point if it is a local maximum or minimum. A table is then constructed containing the decibel level of successive maxima and minima and their frequencies. Each minimum in this table is then tested to determine if it is at least 3.5 dB below the level of its two neighboring maxima, which are, by construction, local maxima. If this test is passed, then the point is labeled as a first approximation to the frequency of a zero in the spectrum. Around that point, a parabola is fitted such that the putative zero and the two neighboring points on the spectrum all fall on the parabola. The actual interpolated frequency where the parabola is a minimum is used as a final estimate of the frequency of the zero. The bandwidth is determined by finding the distance between the two frequencies on either side of the minimum of the zero where the spectrum is 3 dB above the minimum. A typical result of this procedure is to obtain five or six measured zeros and their associated bandwidths in the frequency range up to 22 kHz, as illustrated in FIG. 5.

The next step is to estimate the frequencies of the higher zeros of the spectral list 132. This step is optional, but is preferably performed if well-defined zeros are not located throughout the range of interest, to maximize the accuracy of the calibration function. The estimate of the higher zeros is based on the fact that in an ear canal 23, as in any uniform or conical tube having an abrupt termination, the frequency spacing between the zeros approaches a constant value as the frequencies of the zeros increase.

Figure 6:
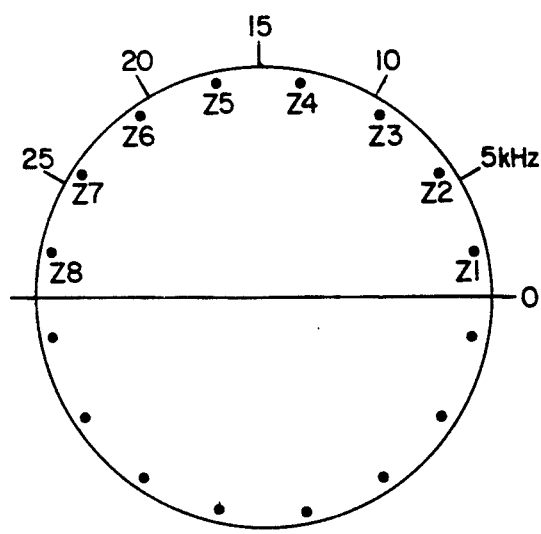
FIG. 6 is a graph of a Z-plane used in extrapolating the higher zeros of the graph of FIG. 5.

As the first step in estimating the frequencies of the higher zeros, the frequency associated with the second zero, which is usually well defined and easy to estimate, is subtracted from the highest zero that can be measured below 22 kHz. That frequency difference is divided by one less than the number of zeros found in that interval to estimate the average spacing between the zeros. Thus, for instance, if the frequencies and bandwidths of the first six zeros are as follows:

|    | Frequency Hz | Bandwidth Hz |
|----|--------------|--------------|
| Z1 | 1850         | 80           |
| Z2 | 5730         | 150          |
| Z3 | 9500         | 220          |
| Z4 | 13060        | 400          |
| Z5 | 16380        | 550          |
| Z6 | 19750        | 770          | the frequencies of the second and sixth zeros are 5730 and 19750 Hz, respectively, and the estimated average spacing is thus $19750 - 5730 \div 4 = 3505$ Hz. The next three zeros are then created by simply adding the average spacing to the highest zero that can be identified. In the present example, this procedure adds zeros as 23255, 26760 and 30265 Hz. The sampling frequency is set equal to the sum of these top two zeros, (57025 Hz, in this example), and the final location of the zeros in the z plane is calculated by extrapolation as shown in FIG. 6.

As the next step in calculating the calibration function for ear canal 23, the spectral non-uniformities created by the interference of the transmitted acoustic pulse with the reflections thereof by eardrum 22 are removed This removal is effected using an all-zero version of the digital resonator algorithm described by B. Gold and L. R. Rabiner in the article "Analysis of Digital and Analog Formant Synthesizers", published in *IEEE Transactions in Audio Electroacoustics*, AU-16, 81-94, Mar., 1968. In the past, this digital resonator algorithm has been used primarily in the analysis of speech signals. This digital resonator algorithm takes the following form:

$$y(nT) = Ax(nT) + By(nT-T) + Cy(nT-2T), \quad (1)$$

where x(nT) are input samples taken from the spectral list 132, y(nT) are samples from the output of the digital resonator, and the constants A, B, and C are related to the frequency F and the bandwidth BW of the zeros as follows:

$C = -\exp(-2PI\ BW\ T)$,
$B = 2\ \exp(-PI\ BW\ T)\cos(2\ PI\ F\ T)$,
$A = 1 - B - C$, where PI is the ratio of the circumference of a circle to its diameter, and T is one over the sampling rate. The variables F and BW are calculated for each zero in the manner discussed above. Each point about the zeros in spectral list 132 is processed through the digital resonator algorithm (1) listed above and then the results are combined so to produce the time domain or coefficient list 136 representing the coefficients of a transversal filter the spectrum of which contains each of the minima or zeros in the spectral list 132.

This filter represents the interference effects between the transmitted acoustic pulse and the reflection of the transmitted acoustic pulse reflected from eardrum 22, as described hereinafter. By combining the spectrum of this filter with spectral list 132, as described below, a calibration function can be generated which relates the amplitude of the excitation signal applied to sound source 26 with the sound pressure of the acoustic sinusoidal signal at the apical end of the ear canal.

Next, the list of coefficients 136 is transformed to the frequency domain by taking the Fourier transform thereof. The resultant list or set 138 illustrated in FIG. 8 identifies the amplitude of each frequency in the coefficient list 136. Preferably, a fast Fourier transform algorithm, e.g., the Cooley-Tukey algorithm, is used in this transformation.

Thereafter, the log power spectra of the spectral lists 132 and 138 is determined.

Figure 8:
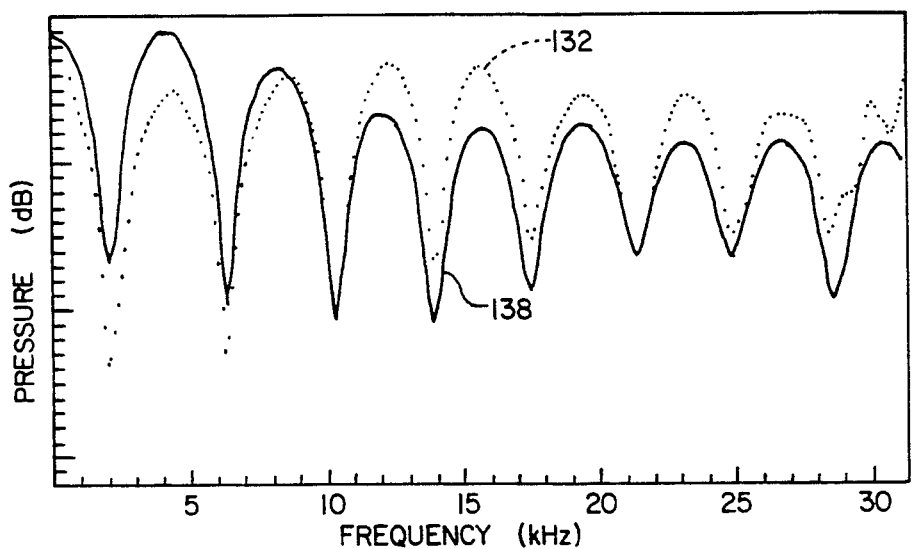
FIG. 8 is a graph of the Fourier transform of the series of coefficients of FIG. 7, with the graph of FIG. 5 being superimposed in phantom.
Figure 9:
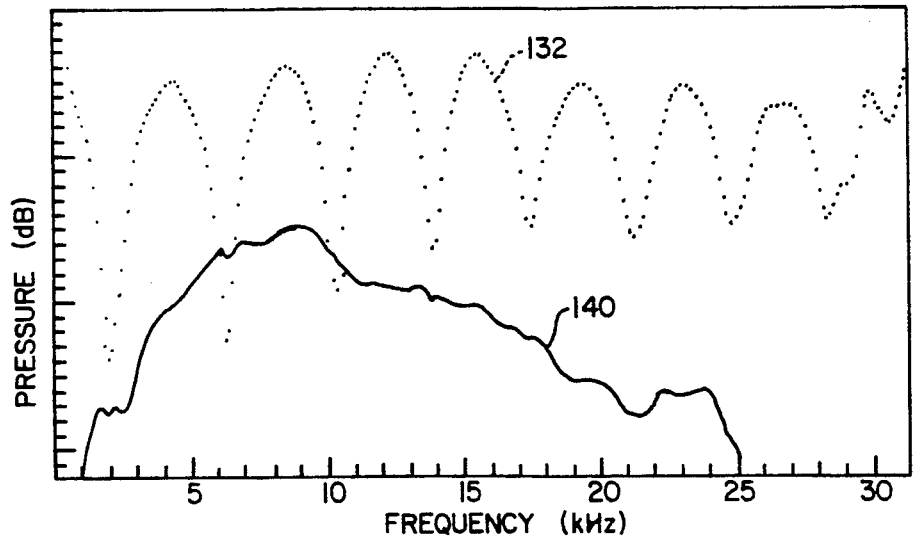
FIG. 9 is a graph of the subtraction of the log power spectrum of the Fourier transform of FIG. 8 from the log power spectrum of the Fourier transform of FIG. 5 which represents the predicted absolute sound pressure level at the eardrum.

As the final step in the calibration function signal-processing procedure, the log power spectrum of spectral list 138 (FIG. 8) is subtracted from the log power spectrum of spectral list 132 so as to produce the resultant spectral list 140 illustrated in FIG. 9. This is equivalent to dividing the lists 132 and 138 in complex linear magnitudes. Alternatively, the inverse of the log power spectrum of list 138 may be added to the log power spectrum of list 132 so as to produce the spectral list 140 illustrated in FIG. 9. This is equivalent to multiplying the list 132 and the reciprocals of list 138 in complex linear magnitudes. As described below, this spectral list 140 constitutes the calibration function for ear canal 23 used in performing high frequency audiometry. As such, the spectral list and the calibration function will both be identified by reference number 140.

Instead of determining the log power spectra of spectral lists 132 and 138 and adding or subtracting the spectra as described above, the spectral list 140 may be calculated by taking the complex values or linear magnitudes constituting the results of the Fourier transforms by which spectral lists 132 and 138 were created, and dividing the corresponding complex values of list 132 by the corresponding complex values of list 138 so as to create spectral list 140.

By the arithmetic operations used to generate spectral list 140, the non-uniformities produced by interference of the transmitted acoustic pulse with the reflection thereof are removed, yielding a signal containing only the effects of non-uniformities produced by the electroacoustic components of the system and the geometry of the ear canal. This resultant signal constitutes a calibration function which can be used to control the output of the sound source 26 during high frequency audiometry. By adjusting the output of the sound source in accordance with the calibration function, acoustic sinusoidal signals can be transmitted into the ear canal 23 so as to have a substantially constant sound pressure level at the apical end of the eardrum regardless of frequency with respect to the excitation signal applied to sound source 26.

The foregoing description of the signal processing procedure for generating spectral list 140 assumes only a single acoustic pulse is used in the procedure. To improve the accuracy of the procedure, however, it is normally desirable to use a train of acoustic pulses, and then average or otherwise combine the time domain lists generated for each of the pulses to provide a single master pulse 140.

High frequency audiometry is performed with the present invention using a sound pressure selection algorithm stored in dynamic memory 112 in computer 110. The algorithm calculates the information to be contained in a control signal that is provided to sound source 26 for triggering the latter to emit selected acoustic sinusoidal signals at sound pressure levels that vary at the point of generation in accordance with the calibration function such that the acoustic sinusoidal signals will be of substantially constant sound pressure level regardless of frequency when the latter intersect the apical end of the eardrum. The algorithm comprises a procedure for increasing or decreasing the amplitude information contained in the control signal provided to sound source 26 based on the calibration function illustrated in FIG. 9.

More specifically, if it is desired to provide a selected acoustic sinusoidal signal at the apical end of the eardrum 22 at a substantially constant pressure level of X dB, each frequency in the selected signal is compared to the corresponding respective frequency in the spectral list 140 (FIG. 9) to determine if the amplitude of the corresponding respective frequency is less than, equal to, or greater than X dB. The amplitude information provided to sound source 26 is then adjusted in accordance with the results of this comparison so that the sound pressure level of the various frequencies in the emitted acoustic sinusoidal signal are such that when the latter reach eardrum 22 their sound pressure level will be the same. Thus, for instance, if at the frequency point f1 on spectral list 140 the amplitude is X+1 dB, then the magnitude of the amplitude information contained in the control signal generated by the algorithm pertaining to frequency f1 will be reduced by 1 dB so that a frequency f1 is generated having an amplitude such that when the frequency f1 reaches the apical end of the eardrum 22 its amplitude will be X dB.

Referring now to FIGS. 1-10, to use the present invention for calculating the calibration function and for performing high frequency audiometry, one end of the lossy waveguide tube 28 is coupled with the distal end of horn 46 and the other end of tube 28 is inserted into counterbore 68 in coupler 60 so as to couple tube 28 in a substantially acoustically-tight manner with the horn 46 and coupler 60. Next, an earpiece tip 64 is selected which will make a substantially acoustically-tight seal with the entrance to the ear canal of interest, while at the same time being relatively comfortable to the individual undergoing high frequency audiometry. This earpiece tip 64 is then mounted on reduced-diameter portion 84. Earpiece tip 64 is made from a resilient material and the outside diameter of portion 84 and the diameter of bore 94 in tip 64 are selected so that earpiece tip 64 will grippingly engage reduced diameter portion 84.

Intermediate section 62 is then threadedly engaged with coupler 60 by inserting threaded portion 80 in threaded bore 70. Preferably, for an ear canal 32 of average length, i.e., 25 mm microphone 34, 34a, or 34b is positioned about 5 cm from apical end 22 of eardrum 24.

Earpiece 30 is then coupled with adjustment fixture 108 of headpiece assembly 104, and tip 64 of earpiece 30 is inserted into the entrance of ear canal 23. Headpiece 106 is then secured around the subject's head, and adjustment fixture 108 is adjusted so that earpiece 30 is securely supported and properly aligned relative to ear canal 23. Headpiece assembly 104 is provided for ensuring that earpiece 30 does not move relative to ear canal 132 during calculation of the calibration function, after calculation of the calibration function and before beginning the high frequency audiometry, and during the high frequency audiometry.

Referring to FIGS. 1-10, prior to performing high frequency audiometry, it is necessary to calculate a calibration function for the ear canal 23 being tested which relates the magnitude of the excitation signal applied to sound source 26 with the sound pressure level at the apical end of the eardrum 22 of the resultant acoustic pulse To begin this calculation, one or more acoustic test pulses are generated at sound source 26 and information contained in reflections of the pulses is used to calculate the calibration function. As illustrated by step 200 in FIG. 10, the duration, amplitude, number, and frequency spectrum of the acoustic pulse(s), which are preferably stored in static memory 114, are accessed using keyboard 128. This information is then provided by control unit 36 to amplifier 40 of sound source 26 over line 126 in the form of an excitation signal. The acoustic pulse preferably has a duration of 10-20 microseconds and includes substantially the entire frequency spectrum in the frequency range 8-20 kHZ with uniform energy per unit frequency.

Upon receipt of this excitation signal, amplifier 40 generates a signal which may be filtered through high-pass filter 42 to remove the low frequency component thereof and is provided to driver 44. Upon receipt of this signal, driver 44 transmits an acoustic pulse having the above-noted amplitude, spectrum and duration characteristics, as illustrated by step 202 in FIG. 10. This pulse is propagated along waveguide tube 28 toward the ear canal 23. Because tube 28 is a lossy waveguide, there is some attenuation of the pulse during its transmission in tube 28.

Figure 10:
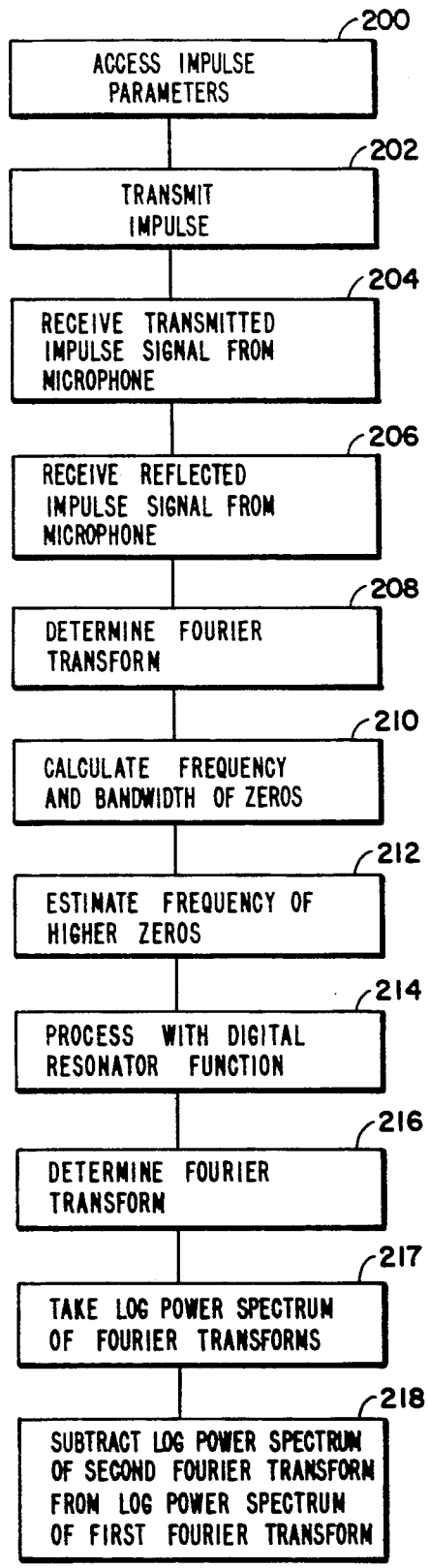
FIG. 10 is a flow chart representation for calculating a calibration function of the ear canal.
Figure 11:
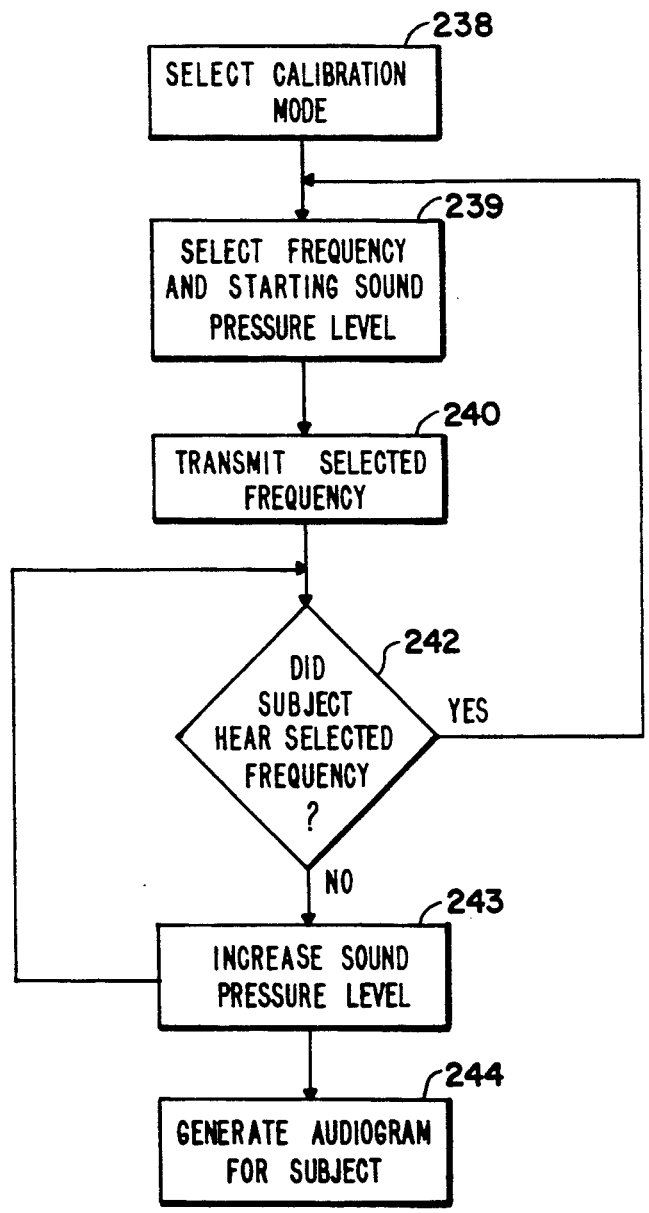
FIG. 11 is a flow chart representation for performing high frequency audiometry.

As the pulse passes by microphone 34, the latter generates an electric signal in response thereto, as illustrated by step 204 in FIG. 10, which constitutes portion 141 of output signal 130 (FIG. 4). This signal is carried over line 124 to control unit 36.

As noted above, as the pulse signal travels through earpiece 30 and ear canal 23, certain irregularities are introduced to the signal by the internal configuration of the earpiece and the ear canal. Interior bores 66 and 86 in earpiece 30 have substantially the same diameter as the inside diameter of tube 28 to minimize introduction of such irregularities.

The pulse then contacts eardrum 22, is reflected by the latter, and is propagated out of the ear canal 23. Irregularities introduced to the original and reflected acoustic pulse arising from the configuration of the ear canal 23 are contained in the reflection of the acoustic pulse. As noted above, these irregularities provide the information from which the calibration function for the ear canal 23 is calculated. In addition, irregularities created by the interference of the transmitted acoustic pulse with the reflected acoustic pulse are contained in the reflected pulse. As noted above, these irregularities obscure those which provide the information from which the calibration function is calculated, and their effect must be removed to implement calibration. As this reflected acoustic pulse passes by microphone 34, 34a or 34b, the latter generates a response signal which is carried over line 124 to control unit 36, as illustrated at step 206 in FIG. 10. This response signal is identified at 142 in FIG. 4.

The inside diameter, length and durometer of tube 28 are selected so that the reflected acoustic pulse, i.e. portion 142 of output signal 130, is attenuated such that substantially none of the reflected acoustic pulse reaches sound source 26, reflects from the latter, and propagates back past microphone 34, 34a, or 34b and into the ear canal 23. By preventing such retransmission of the acoustic pulse, it becomes significantly easier to remove the effects of the interference between the acoustic pulse and the reflection thereof from the response signal received at microphone 34, 34a, or 34b, inasmuch as fewer interference effects are created.

Next, as illustrated by step 208, the Fourier transform of output signal 130 is taken so as to provide the spectral list or set of frequencies identified at 132 in FIG. 5. As described above, the algorithm for taking the Fourier transform, as well as the algorithms for performing the other operations in the signal processing procedure for generating the calibration function are stored in static memory 114 of computer 110 of control unit 36. Output signal 130 is temporarily stored in dynamic memory 112 of unit 36. The Fourier transform calculation is made in the control unit's processor/controller 116 using output signal 130 data from dynamic memory 112 and the Fourier transform algorithm from static memory 114. The result of this calculation is the spectral list 132 illustrated in FIG. 5, which is stored in dynamic memory 112 of control unit 36.

Next, as illustrated at step 210, the frequency and bandwidth of the zeros in spectral list 132 are calculated in the manner described above using an algorithm for performing the same stored in static memory 114 of control unit 36.

Then, as illustrated by step 212, and in the manner described above, an estimate is made of the frequency of the higher zeros in spectral list 132 using an algorithm for performing the same stored in static memory 114 of control unit 36. As noted above, this step can optionally be omitted if well-defined zeros are located throughout the range of interest. However, to improve the accuracy of signal processing procedure, it is preferred that step 212 be performed.

Figure 7:
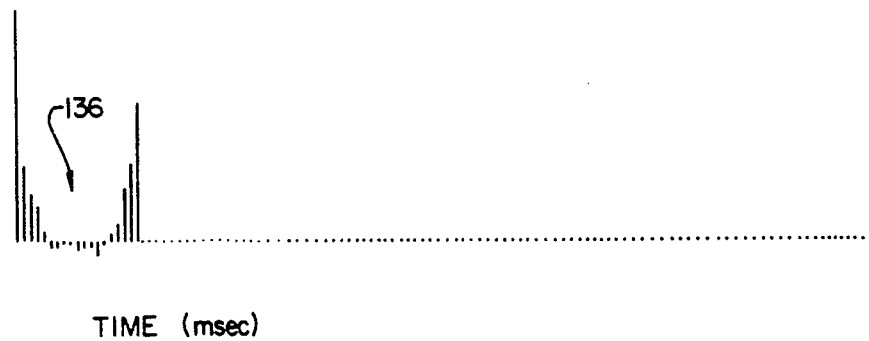
FIG. 7 is a graph of the coefficients calculated from the center frequencies and bandwidths of the minima of the Fourier transform of FIG. 5, achieved by calculation of a digital resonator function.

Next, as illustrated by step 214, the spectral list 132, including the higher zeros thereof calculated at step 212, is processed through a digital resonator function so as to produce the time domain coefficient list 136 illustrated in FIG. 7. The interference effects created by the interference between the transmitted and reflected acoustic pulses will be removed from the output signal generated by microphone 34, 34a, or 34b using this time domain list 136. The digital resonator function is described above and is stored in static memory 114 of control unit 36. List 136 is stored in dynamic memory 112 of control unit 36.

Thereafter, as illustrated by step 216, the Fourier transform of coefficient list 136 is taken so as to produce the spectral list of frequencies 138 of FIG. 8. The algorithm for performing the Fourier transform is stored in static memory 114 of control unit 36 and the spectral list 138 is stored in dynamic memory 112 of control unit 36.

Then, as illustrated by step 217, the log power spectra of spectral lists 132 and 138 are taken using an algorithm for performing the same stored in static memory 114, as described above As the final step in calculating a calibration function for ear canal 23, the inverse of the log power spectrum of spectral list 138 is taken and is added to the log power spectrum of spectral list 132 so as to produce spectral list 140 illustrated in FIG. 9, as illustrated by step 218. Algorithms for taking this inverse and performing this summation are stored in static memory 114 of control unit 36 and spectral list 140 is stored in dynamic memory 112 of the control unit. In the alternative, the log power spectrum of spectral list 138 is subtracted from the log power spectrum of spectral list 132 to provide spectral list 140 using a subtraction algorithm stored in static memory 114.

In place of steps 217 and 218, spectral list 240 may be calculated using complex division, as noted above. That is, the complex values of list 132 are divided by the complex values of list 138.

As noted above, spectral list 140 sets forth by frequency the relationship between the amplitude level of the excitation signal applied to sound source 26 and the sound pressure level of the same acoustic pulse at the apical end 21 of eardrum 22. Inasmuch as the sound pressure level of the acoustic pulse at microphone 34, 34a, or 34b varies directly with the magnitude of the excitation signal provided to sound source 26 from control unit 36, spectral list 140 also indicates the variation in magnitude of the excitation signal that must occur to provide an acoustic sinusoidal signal at substantially the selected sound pressure level at apical end 21 of eardrum 22 regardless of frequency.

The apical end of eardrum 22 is selected as the location in the ear canal at which the sound pressure is determined as it is only at this location where the incoming acoustic pulse does not interact with the reflected acoustic pulse so to produce destructive interference minima. As such, calculation of sound pressure level at any other location along the eardrum 22 or at any other location in the ear canal 23 would be more difficult, inasmuch as the effects of the interference at the specific location chosen would have to be considered in determining the sound pressure level at that location.

Turning now to FIGS. 1–11, the present invention may also be used to perform high frequency audiometry using the calibration function 140 obtained by the procedure illustrated in FIG. 10. It is critical that the same sound source 26, tube 28, earpiece 30, and microphone 34 or 34a be used for performing the high frequency audiometry as was used in generating the calibration function 140. Moreover, it is critical that the entire apparatus not be moved or disturbed in any way between completion of the calibration function calculation procedure and commencement of the high frequency audiometry As noted above, headpiece assembly 104 is provided for ensuring such movement is avoided.

After obtaining the calibration function for ear canal 23 and prior to beginning high frequency audiometry at each frequency, control unit 36 is placed in the calibration mode via keyboard 128, as illustrated by step 238 By placing control unit 36 in this mode, the latter is instructed to vary the amplitude information in the control signal transmitted to sound source 26 in accordance with an algorithm for performing the same which uses the calibration function 140 of FIG. 9, so as to cause the sound pressure level of the range of acoustic frequencies generated by sound source 26 to vary so that the sound pressure level of the frequencies reaching the eardrum 22 is substantially the level selected by the user of the system 20. Next as illustrated by step 239 a frequency and starting sound pressure level is selected.

The excitation signal is then transmitted to sound source 26, as illustrated by step 240, so as to cause the latter to generate the sinusoidal signal at the frequency and sound pressure level selected in step 239. The subject's ability to hear the selected frequency of sound in the acoustic sinusoidal signal at the first sound pressure level is monitored, as illustrated by step 242. This monitoring can be done, for instance, using an electrical signaling device (not shown) coupled to control unit 36 which the subject depresses when the sound is heard and releases when the sound is not heard. If the subject does not hear the sound, the sound pressure level is increased, as illustrated by step 243, and a new acoustic sinusoidal signal is generated. This process is repeated until the subject hears the test sound, at which point the process returns to step 239 where a new frequency is selected. An acoustic sinusoidal signal at the new frequency is then generated at the starting sound pressure level, and the sound pressure level at which the subject can first hear the new frequency is established in the manner described above. This process is then repeated for a selected range of frequencies.

Control unit 36 can be easily programmed, as is well known in the art, to generate a list for each frequency transmitted to the subject's ear canal identifying the sound pressure level at which the subject first hears the frequency. This list is generated by tabulating the values of the hearing sensitivity thresholds found for each frequency so as to provide an audiogram or hearing sensitivity profile which describes the subject's absolute hearing threshold for each frequency in the range of interest. This list generation step is identified as step 244 in FIG. 11.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. A system for determining the sound transmission characteristics of a human ear canal, the system comprising:
   sound source means for generating an acoustic signal containing a plurality of frequencies above 2 kHz;
   hollow elongate means coupled to said sound source means and adapted to be coupled to the entrance to the ear canal for forming, together with said ear canal, a lossy, substantially closed acoustic transmission line between said sound source means and the eardrum in said ear canal, for propagating said acoustic signal from said sound source means into said ear canal and for absorbing the reflections of said acoustic signal from the interior of the ear canal so as to substantially prevent said reflections from the propagating back to said sound source means, reflecting off the latter, and propagating back into said ear canal; and
   microphone means disposed adjacent said ear canal entrance for measuring the sound pressure in said transmission line of said acoustic signal and said reflections of the acoustic signal.

2. A system according to claim 1, the system further comprising:
   calculating means connected to said microphone means for calculating a calibration function for the ear canal based on the sound pressure measured by said microphone means.

3. A system according to claim 2, wherein said acoustic signal generated by said sound source means comprises a plurality of frequencies each having an associated amplitude, and said sound source means generates said acoustic signal upon receipt of an excitation signal having a corresponding respective plurality of frequencies each having an associated amplitude, wherein said calculating means comprises:
   first transform means for determining the Fourier transform of said sound pressure measured by said microphone means so as to produce a first set of amplitudes each at a unique respective frequency, wherein several of said amplitudes define minima or zeros in said Fourier transform.

4. A system according to claim 3, wherein said calculating means further comprises:

means for calculating the center frequency and bandwidth of each of said minima or zeros.

5. A system according to claim 4, wherein said calculating means further comprises:
synthesis means for synthesizing from the frequency and bandwidth of each of said minima or zeros a time domain coefficient list representing the coefficients of a transversal filter the spectrum of which contains each of said minima or zeros.

6. A system according to claim 5, wherein said calculating means further comprises:
second transform means for determining the Fourier transform of said coefficient list so as to produce a second set of amplitudes each at a unique frequency, wherein several of said amplitudes define minima or zeros in said Fourier transform.

7. A system according to claim 6, wherein said calculating means further comprises:
log means for evaluating the log power spectrum of said first set and said second set.

8. A system according to claim 7, wherein said calculating means further comprises:
means for subtracting said log power spectrum of said second set from said log power spectrum of said first set so as to create a frequency domain calibration list relating the amount by which the amplitude of each frequency in said acoustic signal at the apical end of said eardrum is increased or decreased relative to the amplitude of the corresponding respective frequency of said excitation signal.

9. A system according to claim 2, wherein said acoustic signal generated by said sound source means comprises a plurality of frequencies each having an associated amplitude, and said sound source means generates said acoustic signal upon receipt of an excitation signal having a corresponding respective plurality of frequencies each having an associated amplitude, wherein said calculating means comprises:
means for creating a frequency domain calibration list using said sound pressures measured by said microphone means relating the amount by which the amplitude of each frequency in said acoustic signal at the apical end of said eardrum is increased or decreased relative to the amplitude of the corresponding respective frequency of said excitation signal.

10. A system according to claim 2, wherein said acoustic signal generated by said sound source means comprises a plurality of frequencies each having an associated amplitude, and said sound source means generates said acoustic signal upon receipt of an excitation signal having a corresponding respective plurality of frequencies each having an associated amplitude, wherein said calculating means comprises:
means for generating a filter representing the interference effects in said sound pressures measured by said microphone means created by interaction between said acoustic pulse and said reflections of said acoustic signal in said ear canal; and
means for combining said filter with said sound pressures measured by said microphone means so as to create a frequency domain calibration list relating the amount by which the amplitude of each frequency in said acoustic signal at the apical end of said eardrum is increased or decreased relative to the amplitude of the corresponding respective frequency of said excitation signal.

11. A system according to claim 10, wherein said means for generating comprises:
means for locating minima amplitudes in said sound pressures measured by said microphone means;
means for calculating the center frequency and bandwidth of each of said minima amplitudes;
wherein said means for generating generates said filter using said center frequency and bandwidth of each said minima amplitudes.

12. A system according to claim 2, wherein said acoustic signal generated by said sound source means comprises a plurality of frequencies each having an associated amplitude, and said sound source means generates said acoustic signal upon receipt of an excitation signal having a corresponding respective plurality of frequencies each having an associated amplitude, wherein said calculating means comprises:
first transform means for determining the Fourier transform of said sound pressured measured by said microphone means so as to produce a first set of amplitudes each at a unique respective frequency, wherein several of said amplitudes define minima or zeros in said Fourier transform;
means for calculating the center frequency and bandwith of each of said minima or zeros;
synthesis means for synthesizing from the frequency and bandwidth of each of said minima or zeros a time domain coefficient list representing the coefficients of a transversal filter the spectrum of which contains each of said minima or zeros;
second transform means for determining the Fourier transform of said coefficient list so as to produce a second set of amplitudes each at a unique frequency, wherein several of said amplitudes define minima or zeros in said Fourier transform;
means for combining said first set with said second set so as to create a frequency domain calibration list relating the amount by which the amplitude of each frequency in said acoustic signal at the apical end of said eardrum is increased or decreased relative to the amplitude of the corresponding respective frequency of said excitation signal.

13. A system according to claim 12, wherein said means for calculating further comprises extrapolation means for (1) adding three or more minima or zeros to said first set at frequencies that are higher than the frequency of the highest-frequency minima or zero in said several minima or zeros, wherein the frequency at which each of said three or more minima or zeros is located is determined by extrapolation using the frequency and bandwidth of said minima or zeros calculated by said means for calculating and (2) assigning an arbitrary bandwidth to each of said three or more minima or zeros.

14. A system according to claim 12, wherein said means for combining comprises:
means for determining the complex linear magnitudes of said first set and said second set and for dividing said complex linear magnitudes of the first set by said complex linear magnitudes of the second set so as to create said frequency domain calibration list.

15. A system according to claim 12, wherein said means for combining comprises:
log means for evaluating the log power spectra of said first set and said second set; and
means for subtracting said log power spectrum of second set from said log power spectrum of said first set so as to create said frequency domain calibration list.

16. A system according to claim 1, wherein said sound source means comprises an amplifier, a high-pass filter, and a transducer.

17. A system according to claim 1, wherein said hollow elongate means comprises absorption means disposed adjacent said sound source means for absorbing said reflections so as to substantially prevent said reflections from propagating back to said sound source means, reflecting off the latter, and propagating back into said ear canal.

18. A system according to claim 17 wherein said absorption means comprises absorbent cotton.

19. A system according to claim 1, wherein said hollow elongate means comprises means for enclosing a fluid acoustic propagation medium through which said acoustic signal will propagate.

20. A system according to claim 19, wherein said absorption means comprises absorptive foam.

21. A system according to claim 19, wherein said absorption means comprises urethane foam.

22. A system according to claim 1, wherein said hollow, elongate means further comprises:
a resilient, elongate tube having (1) a distal end, (2) a proximal end that is coupled to said sound source means and (3) a hollow interior, said tube having a length, inside diameter and acoustic impedance selected so as to permit (a) said acoustic signal to propagate in said hollow interior from said proximal end to said distal end and (b) said reflections of said acoustic signal to propagate in said hollow interior from said distal end to said proximal end, reflect off said sound source means, and propagate back toward said distal end with attenuation so as to be substantially attenuated before reaching said proximal end.

23. A system according to claim 22, wherein the inside diameter of said hollow interior is smaller at said distal end than at said proximal end.

24. A system according to claim 23, wherein the inside diameter of said hollow interior at said distal end is approximately equal to the inside diameter of said ear canal at the entrance thereto.

25. A system according to claim 22, wherein said hollow, elongate means further comprises:
ear piece means coupled with said distal end of said tube and adapted to be coupled to said ear canal entrance for (1) providing a substantially acoustically-continuous acoustic transmission line between said tube and said ear canal, (2) supporting said microphone means adjacent said ear canal entrance, and (3) transmitting said acoustic signal from said distal end of said tube to said entrance of said ear canal and transmitting said reflections of said acoustic signal from said entrance of said ear canal to said distal end of said tube.

26. A system according to claim 25, wherein said earpiece means comprises a housing assembly having a cylindrical interior in which said acoustic signal and said reflections of said acoustic signal are transmitted, said cylindrical interior having an inside diameter that is substantially identical to the inside diameter of said tube.

27. A system according to claim 25, wherein said earpiece means comprises a housing assembly having a cylindrical interior in which said acoustic pulse and said reflections of said acoustic pulse are transmitted, said cylindrical interior having a first end and a second, further wherein said cylindrical interior tapers from said first end to said second end and the inside diameter of said second end is substantially equal to the inside diameter of said ear canal at the entrance thereto.

28. A system according to claim 26, wherein said housing assembly further comprises a resilient tip adapted to be coupled with the entrance of said ear canal so as to achieve a substantially acoustically-tight seal therewith.

29. A system according to claim 26, wherein said microphone means is secured to said housing assembly inside said cylindrical interior thereof.

30. A system according to claim 26, wherein said housing assembly comprises an aperture extending therethrough, further wherein said microphone means is secured to said housing assembly longitudinally within and radially outside said cylindrical interior thereof and is acoustically coupled with said cylindrical interior via said aperture.

31. A system according to claim 30, wherein said microphone means has a diaphragm and said microphone means is secured to said housing assembly so that said diaphragm is substantially coextensive with said cylindrical interior and is positioned at the junction of said aperture and said cylindrical interior.

32. A system according to claim 30, wherein said microphone means has a diaphragm and said microphone means is secured to said housing assembly so that said diaphragm is spaced outwardly from said cylindrical interior.

33. A system according to claim 32, wherein said housing assembly comprises acoustic port means disposed in said aperture for acoustically coupling said diaphragm of said microphone means with said cylindrical interior.

34. A system according to claim 33, wherein said acoustic port means is acoustically compensated with respect to said microphone means so that substantially no non-uniformities are introduced into said acoustic signal and said reflections of said acoustic pulse when measured by said microphone means.

35. A system according to claim 22, wherein said tube has a length of approximately 650 mm, an inside diameter of approximately 6.35 mm, and an acoustic impedance of approximately 125 acoustic ohms in CGS units.

36. A system according to claim 22, wherein the length of said microphone means, as measured along any axis thereof, is less than half the diameter of said hollow interior of said tube.

37. A system according to claim 1, wherein said hollow, elongate means further comprises (1) a first elongate tube having a first end that is coupled with said sound source means, a second end, and a hollow interior and (2) a second, elongate tube having a first end, and a second end that is coupled to said second end of said first tube, and a hollow interior, said first and second tubes each having a length, inside diameter and acoustic impedance selected so that said coupled tubes will permit (a) said acoustic signal to propagate in said hollow interiors of said first and second tubes from said first end of said first tube to said first end of said second tube, and (b) said reflections of said acoustic signal to propagate in said hollow interiors of said first and second tubes from said first end of said second tube to said first end of said first tube, reflect off said sound source, and propagate back toward said first end of said second tube with attenuation so as to be substantially attenuated before reaching said first end of said second tube.

38. A system according to claim 1, wherein said hollow, elongate means comprises a resilient, elongate tube having (1) a distal end, (2) a proximal end that is coupled to said sound source means and (3) a hollow interior, said tube having an inside diameter approximately equal to that of said ear canal at the entrance thereto, and a length selected so that the acoustic impedance of said tube is approximately equal to $\rho c/A$, where $\rho$ is the density of air, c is the velocity of sound, and A is the area of the cross section of said hollow interior of said tube.

39. A system according to claim 1, further comprising headpiece means coupled to said hollow, elongate means and adapted to be coupled to the head of the subject in which said ear canal is located for supporting said hollow, elongate means in a predetermined, substantially fixed relationship relative to said ear canal.

40. A system according to claim 1, wherein said microphone means has an essentially flat frequency response for frequencies ranging from at least 3 kHz to at least 25 kHz.

41. A method of calculating a calibration function for an ear canal that correlates the (1) amplitude of each frequency in an excitation signal provided to a device for generating an acoustic signal containing a plurality of frequencies above 2 KHz and transmitting the latter into the ear canal to (2) the amplitude of the corresponding respective frequency of said acoustic signal at the apical end of the eardrum of the ear canal, for use in a method of providing high frequency sound at a predetermined amplitude at the apical end of the eardrum of the ear canal for all frequencies of interest, the method comprising in sequence the steps of:
generating an excitation signal having a plurality of frequencies each of which has an associated amplitude;
transducing said excitation signal at a location distant from said ear canal into an input acoustic signal having a corresponding respective plurality of frequencies each of which has an associated amplitude;
transmitting the input acoustic signal to the entrance of the ear canal so as to permit the input acoustic signal to enter the ear canal and be reflected by the eardrum in the ear canal and thereby create an output acoustic signal, said output acoustic signal containing non-uniformities created by (1) interference of said input acoustic signal with said output acoustic signal, (2) the configuration of the ear canal and (3) spectral errors created in said generating, transducing, and transmitting steps; representing the coefficients of a transversal filter the spectrum of which contains each of said plurality of minima;
taking the Fourier transform of said time domain coefficient list so as to produce a second list of the amplitudes of each frequency in said time domain list; and
combining said first list and said second list so as to create said stripped spectrum.

42. A method according to claim 41, wherein said removing step comprises:
taking the Fourier transform of said recorded input and output signals so as to produce a first list of amplitudes of each frequency contained in said recorded input and output signals, said amplitudes defining a plurality of minima each of which is located at a unique frequency;
calculating the center frequency and bandwidth of each of said plurality of minima;
synthesizing a time domain coefficient list, using said center frequency and bandwidth of said plurality of minima,
attenuating the output acoustic signal so as to substantially prevent the latter from propagating back to said location distant from the entrance of the ear canal, reflecting at said distant location, and propagating back into said ear canal;
detecting, adjacent the entrance of the ear canal, and recording said input acoustic signal and said output acoustic signal; and
removing from the spectra of the recorded input and output acoustic signals said non-uniformities arising from interference between the input and output acoustic signals so as to provide a stripped spectrum containing said non-uniformities created by said configuration of the ear canal and said spectral errors.

43. A method according to claim 42, wherein said combining step further comprises the steps of:
taking the log power spectrum of said first list and said second list; and
subtracting said long power spectrum of said second list from said log power spectrum of said first list so as to create said stripped spectrum.

44. A method according to claim 41, further comprising the step of selecting the distance between the location where said acoustic signal is generated and said entrance of the ear canal so that said distance is at least five times the distance between said entrance to said ear canal and the eardrum of said ear canal.

45. A system for providing acoustic sinusoidal signals of selected frequencies and at selected sound pressure levels at the apical end of the eardrum of an ear canal, the system comprising:
(A) calibration means for determining the sound transmission characteristics of an ear canal based on information contained in an acoustic calibration signal having a plurality of frequencies greater than 2 KHz transmitted into said ear canal and the reflection thereof, said calibration means comprising:
sound source means for generating said acoustic calibration signal and said acoustic sinusoidal signals;
hollow elongate means coupled to said sound source means and coupled to the entrance to the ear canal for forming, together with said canal, a lossy, substantially closed acoustic transmission line between said sound source means and the eardrum in said ear canal, for propagating said acoustic calibration signal and said acoustic sinusoidal signals from said sound source means into said ear canal and for absorbing the reflections of said acoustic calibration signal and said acoustic sinusoidal signals so as to substantially prevent said reflections from propagating back to said sound source means, reflecting from the latter, and propagating back to said entrance to the ear canal;
microphone means disposed adjacent said ear canal entrance for measuring the sound pressure in said transmission line of said acoustic calibration signal and said reflections thereof; and calculating means connected to said microphone means for calculating a calibration function for the ear canal based on the sound pressure measured by said microphone means; and (B) selection means coupled to said sound source means for selecting said selected frequencies and said selected sound pressure levels of said acoustic sinusoidal signals in accordance with said calibration function so that the selected sound pressure level of said acoustic sinusoidal signals at said apical end of the eardrum is substantially at a predetermined level regardless of frequency.

46. A system according to claim 45, wherein said hollow elongate means comprises absorption means disposed adjacent said sound source means for absorbing said reflections so as to substantially prevent said reflections from propagating back to said sound source means, reflecting off the latter, and propagating back into said ear canal.

47. A system according to claim 45, wherein said hollow, elongate means further comprises:

a resilient, elongate tube having (1) a distal end, (2) a proximal end that is coupled to said sound source means and (3) a hollow interior, said tube having a length, inside diameter and acoustic impedance selected so as to permit (a) said acoustic calibration signal and said acoustic sinusoidal signals to propagate in said hollow interior from said proximal end to said distal end and (b) said reflections of said acoustic calibration signal and said acoustic sinusoidal signals to propagate in said hollow interior from said distal end to said proximal end, reflect off said sound source means, and propagate back toward said distal end with attenuation so as to be substantially attenuated before reaching said proximal end.

48. A system according to claim 45, wherein said hollow, elongate means comprises a resilient, elongate tube having (1) a distal end, (2) a proximal end that is coupled to said sound source means and (3) a hollow interior, said tube having an inside diameter approximately equal to that of said ear canal at the entrance thereto, and a length selected so that the acoustic impedance of said tube is approximately equal to $\rho c/A$, where $\rho$ is the density of air, c is the velocity of sound, and A is the area of the cross section of said hollow interior of said tube.

49. A system according to claim 47, wherein said hollow, elongate means further comprises:

earpiece means coupled to said distal end of said tube and said ear canal entrance for (1) providing a substantially acoustically-continuous acoustic transmission line between said tube and said ear canal, (2) supporting said microphone means adjacent said ear canal entrance, and (3) transmitting said acoustic calibration signal and said acoustic sinusoidal signals from said distal end of said tube to said entrance of said ear canal and transmitting said reflections of said acoustic calibration signal and said acoustic sinusoidal signals from said entrance of said ear canal to said distal end of said tube.

50. A system according to claim 45, further comprising headpiece means coupled to said hollow, elongate means and adapted to be coupled to the head of the subject in which said ear canal is disposed for supporting said hollow, elongate mans in a predetermined, substantially fixed relationship relative to said ear canal.

51. A system according to claim 45, wherein said acoustic calibration signal generated by said sound source means comprises a plurality of frequencies each having an associated amplitude, and said sound source means generates said acoustic calibration signal upon receipt of an excitation signal having a corresponding respective plurality of frequencies each having an associated amplitude, wherein said calculating means comprises:

first transform means for determining the Fourier transform of said sound pressure measured by said microphone means so as to produce a first set of amplitudes each at a unique respective frequency, wherein several of said amplitudes define minima or zeros in said Fourier transform;

means for calculating the center frequency and bandwidth of each of said minima or zeros;

synthesis means for synthesizing from the frequency and bandwith of each of said minima or zeros a time domain coefficient list representing the coefficients of a transveral filter the spectrum of which contains each of said minima or zeros;

second transform means for determining the Fourier transform of said coefficient list so as to produce a second set of amplitudes each at a unique frequency, wherein several of said amplitudes define minima or zeros in said Fourier transform;

means for combining aid first set with said second set so as to create a frequency domain calibration list relating the amount by which the amplitude of each frequency in said acoustic calibration signal at the apical end of said eardrum is increased or decreased relative to the amplitude of the corresponding respective frequency of said excitation signal.

52. A system according to claim 51, wherein said means for combining comprises:

log means for evaluating the log power spectra of said first set and said second set; and means for subtracting said log power spectrum of said second set from said log power spectrum of said first set so as to create said frequency domain calibration list.

53. A system according to claim 51, wherein said means for combining comprises:

means for determining the complex linear magnitudes of said first set and said second set and for dividing said complex linear magnitudes of the first set by said complex linear magnitudes of the second set so as to create said frequency domain calibration list.

54. A system according to claim 45, wherein said acoustic calibration signal generated by said sound source means comprises a plurality of frequencies each having an associated amplitude, and said sound source means generates said acoustic calibration signal upon receipt of an excitation signal having a corresponding respective plurality of frequencies each having an associated amplitude, wherein said calculating means comprises:

means for creating a frequency domain calibration list using said sound pressures measured by said microphone means relating the amount by which the amplitude of each frequency in said acoustic calibration signal at the apical end of said eardrum is increased or decreased relative to the amplitude of the corresponding respective frequency of said excitation signal.

55. A system according to claim 45, wherein said acoustic calibration signal generated by said sound source means comprises a plurality of frequencies each having an associated amplitude, and said sound source means generates said acoustic calibration signal upon receipt of an excitation signal having a corresponding respective plurality of frequencies each having an associated amplitude, wherein said calculating means comprises:

means for generating a filter representing the interference effects in said sound pressures measured by said microphone means created by interaction between said acoustic calibration signal and said reflections of said acoustic calibration signal in said ear canal; and means for combining said filter with said sound pressures measured by said microphone means so as to create a frequency domain calibration list relating the amount by which the amplitude of each frequency in said acoustic calibration signal at the apical end of said eardrum is increased or decreased relative to the amplitude of the corresponding respective frequency of said excitation signal.

* * * * *